(12) United States Patent
Ahmad et al.

(10) Patent No.: US 7,560,578 B2
(45) Date of Patent: Jul. 14, 2009

(54) PALM-BASED HYDROXY FATTY ACID

(75) Inventors: Salmiah Ahmad, Kajang (MY); Soi Seng Hoong, Kajang (MY); Mohd Norhisham Sattar, Kajang (MY); Yusrabbil Amiyati Yusof, Kajang (MY); Hazimah Abu Hassan, Kajang (MY); Roila Awang, Kajang (MY)

(73) Assignee: Malaysian Palm Oil Board (MY)

( * ) Notice: Subject to any disclaimer, the term of this patent is extended or adjusted under 35 U.S.C. 154(b) by 795 days.

(21) Appl. No.: 10/974,815

(22) Filed: Oct. 28, 2004

(65) Prior Publication Data
US 2005/0240041 A1 Oct. 27, 2005

(30) Foreign Application Priority Data
Apr. 21, 2004 (MY) .............................. PI 2004 1450

(51) Int. Cl.
*C07C 51/16* (2006.01)
(52) U.S. Cl. ...................................... 554/138; 554/132
(58) Field of Classification Search .................. 554/132, 554/138
See application file for complete search history.

(56) References Cited

U.S. PATENT DOCUMENTS 2,443,280 A * 6/1948 Swern et al. ................. 554/138

OTHER PUBLICATIONS

WPIDS Abst. of EP-974,639, 2000.*
WPIDS Abstr. DE-4,332,292, 1995.*

* cited by examiner

*Primary Examiner*—Deborah D Carr
(74) *Attorney, Agent, or Firm*—Dicke, Billig & Czaja, PLLC

(57) ABSTRACT

The present invention relates to an improved process for producing hydroxy fatty acids preferably dihydroxy or polyhydroxy acids from unsaturated fatty acids derived from natural oils and fats. The unsaturated fatty acids extracted from natural vegetable oils or animal fats preferably palm-based oleic acid is hydroxylated or oxidized by peracetic acid which formed in situ from a mixture of hydrogen peroxide and formic acid. The process for producing dihydroxy or polyhydroxy fatty acids according to the present invention involve less cost, easier to perform and reduced reaction time. In addition, the dihydroxy or polyhydroxy acids produced according to the present invention is non irritant and suitable to be used in production of cosmetic products.

8 Claims, No Drawings

PALM-BASED HYDROXY FATTY ACID

FIELD OF THE INVENTION

The present invention relates to a process for producing hydroxy fatty acids from natural oils and fats. More particularly, the present invention relates to a process for producing hydroxy fatty acids by hydroxylation or oxidation of unsaturated fatty acids derived from vegetable oils or animal fats.

BACKGROUND OF THE INVENTION

Certain oxidizing agents or oxidants convert alkenes such as unsaturated fatty acids into compounds known as glycols. Glycols are simply dihydroxy alcohols; their formation amounts to the addition of two hydroxyl groups to the double bond. Of the numerous oxidants that caused hydroxylation, two of the most commonly used are cold alkaline potassium permanganate ($KMnO_4$) and peroxyacid such as performic acid. Permanganate oxidation on unsaturated fatty acids usually give vic-diols (cis) in high yield as shown in the equation below. Oxidation or sometimes known as hydroxylation of unsaturated fatty acids will lead to di- and polyhydroxy acids depending on the number of unsaturated present in the acids.

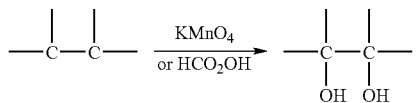

According to the MERCK index, one of the dihydroxy acid, 9,10-dihydroxystearic acid (DHSA) of molecular weight 316.18 and molecular formula of $CH_3(CH_2)_7$ $CHOHCHOH(CH_2)_7COOH$ is white, odorless, tasteless and lustrous crystal with fatty feel. It is insoluble in water, soluble in hot alcohol or acetone and slightly soluble in ether and has a melting point of 132-136° C. The compound is also reported to find applications in the manufacturing of cosmetic and toilet preparations.

According to U.S. Pat. No. 2,443,280, 9,10-dihydroxystearic acid is produced by conversion of oleic acid with a mixture of hydrogen peroxide and acetic acid as well as catalytic quantities of a strong acid such as sulphuric acid. The hydroxy acetoxy acid developing thereby is regenerated afterwards by soaping with the following decomposition to 9,10-dihydroxystearic acid.

In EP0025940 the production of dihydroxystearic acid is described on the basic of oleic acid, whereby 1 mol of oleic acid is mixed with 4 mole formic acid and to this mixture 1.1 mole of the oxidizing agent hydrogen peroxide is added in the 1 hour process with 50° C. is admitted. The conversion product must be soaped with caustic soda solution and be split afterwards with concentrated hydrochloric acid.

DE4332292 disclosed that hydroxylation of unsaturated carboxylic acids with a hydrogen peroxide and formic acid and/or acetic acid at temperature from 25° C. to 90° C. The reaction required less quantity of catalyst but needs longer response time than EP0025940.

Methods on the production of di- and polyhydroxy fatty acids from mono- or polyunsaturated fatty acid usually in oxidant-catalyst environment such as selenium oxide-tert-butyl hydroperoxide, hydrogen peroxide-tungtic acid, ruthenium and osmium tetroxides. The resultant epoxides are normally hydrolyzed or catalytically opened by adding acetic acid (U.S. Pat. No. 2,443,280) or formic acids (U.S. Pat. No. 4,101,589 and European patent 0025944031). In another U.S. Pat. No. 4,851,593), poly or di-hydroxy fatty acid can be obtained from polymerization of fatty acids in liquid phase reaction at temperature of 260° C. to 343° C. (500° F. to 650° F.), pressure of up to 1000 psi in the presence of a hydrogenation catalyst. These systems however have some disadvantages such as over-oxidation which led to cleavage products, tedious removal of reduced oxidants or the chemicals used were expensive and toxic.

It was also reported that natural hydroxy fatty acids are mostly obtained from the ricinoleic acid present in abundance (~90%) in castor oil.

SUMMARY OF THE INVENTION

Therefore an object of the present invention is to provide a method to produce hydroxy fatty acids preferably di- or polyhydroxy fatty acids from natural fats and oils preferably from palm-based oleic acid.

Oleic acid or 9-octadecenoic acid present in other oil and fats such as 50% in tallow, 45% in tall oil and about 40% in palm oil, is an alternative source for polyhydroxy fatty acids. Thus, besides oleic acid the other feedstocks of animal or vegetable based oils and fats and their derivatives can also be used to produce mono-, di- and polyhydroxystearic acids in the present invention.

Another object of the present invention is to provide an improved method to produce di- or polyhydroxy fatty acids by reacting unsaturated fatty acids with performic acid produced in-situ with 98% of yield.

A further object of the present invention is to provide a method to produce di- or polyhydroxy fatty acid involve less cost, easier to perform and reduced reaction time.

Still another object of the present invention is to prepare a di- or polyhydroxy fatty acid that is non irritant and suitable to be used in cosmetic products.

Another object of the present invention is to provide a method to purifying crude di- or polyhydroxy fatty acids.

Palm oleic acid is mainly made-up of 70-75% oleic acid and about 10-1-5% linoleic acid. Earlier investigation by the inventors of the present invention have indicated that palm-based dihydroxystearic acid or 9,10-dihydroxystearic acid (palm-DHSA) exhibited some differences in its physical properties. Palm oleic acid consists of mainly C18:1 (73.9%) and C18:2 (15.3%). The rest makes up about 10 percent. Under similar reaction conditions, linoleic acid (C18:2) will yield tetra-hydroxystearic acid.

The present invention relates to an improved process to produce hydroxy fatty acid preferably dihydroxy or polyhydroxy fatty acids using unsaturated fatty acids preferably palm-based oleic acid from performic acid produced in-situ. The repeated trials by inventors at laboratory scales (<10 L) and pilot plant scales (<800 Kg) have shown that oleic acid hydroxylated or oxidized by performic acid in-situ, in the presence of hydrogen peroxide and a catalytic amount of concentrated sulphuric acid yield more than 98% of dihydroxy or polyhydroxy acids, based on the unsaturation of the starting oleic acid. The overall reaction time was reduced to between four to six hours before at least about 95% of crude dihydroxy or polyhydroxy could be obtained.

It is also observed that the melting point of palm DHSA produced according to the present invention is lower and falls in the range of about 85-92° C., even after conditioning it under low humidity environment (dessicator in the presence of blue silica gel) for two weeks. The melting point of DHSA as reported in MERCK is 132-135° C.

The crude DHSA could be purified and recrystalized in solvents like short chained alcohols such as ethanol and isopropanol (IPA) with or without water.

The purified palm DHSA obtained in the laboratory was subjected to in-vitro and in-vivo dermal irritection test which confirmed that the compound is non irritant, and thus suitable as one of the ingredients used in cosmetic products. The details of the current invention is described below.

DETAILED DESCRIPTION OF INVENTION

The present invention relates to an improved process of producing hydroxy fatty acid preferably dihydroxy or polyhydroxy fatty acids from natural fats and oils. Dihydroxy fatty acid preferably 9,10-dihydroxystearic acid (DHSA) is produced from palm-based oleic acid according to the present invention. The following is reaction scheme of the invention:

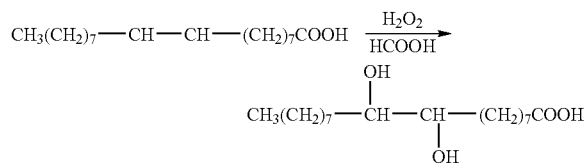

Commercially available palm-based oleic acids or oleic acids derived from other oils or fats are seldom in high purity state. Besides oleic acid (C18:1), they also contain saturated fatty acids of various chain lengths (C8, C10, C12, C14, C16, C18 and C20), plus other unsaturated fatty acids especially linoleic (C18:2) and linolenic (C18:3), present in various percentages. The fatty acid composition of oleic acid and the products of the reactions can be determined by gas chromatography. Other chemical characteristics used to identify the products are via hydroxyl value (AOCS Method Cd 13-60) and acid value (AOCS Method Te 1a-64). Table 1 shows the characteristic of palm-based oleic acid produced in Malaysia.

TABLE 1

Characteristics of palm-based oleic acid produced in Malaysia

| Parameter | Range |
| --- | --- |
| Fatty Acids Composition | |
| C8:0 | 0.1-0.8 |
| C10:0 | Trc-1.2 |
| C12:0 | 0.9-2.4 |
| C14:0 | 0.3-1.5 |
| C16:0 | 3.1-5.5 |
| C16:1 | 0.1-0.3 |
| C18:0 | 1.2-7.6 |
| C18:1 | 71.4-78.0 |
| C18:2 | 11.8-17.3 |
| C18:3 | Trc-0.6 |
| C20:0 | 0.1-0.5 |
| Others | To 100 |
| Iodine Value (g $I_2$/100 g) | 87-95 |
| Acid Value (mgKOH/g) | 180-204 |

*Trc—Traces

Hydroxylation of unsaturated palm based fatty acids with formic acid/hydrogen peroxide is applied in the present invention. The use of formic acid/hydrogen peroxide as an oxidant has an advantage because the chemicals are inexpensive compared to other oxidants or catalysts. The oxidation process can be carried out under mild and controlled conditions, thus reducing the possibility of over oxidation.

According to the present invention, the ratios between the reactants play an important role in determining the yield of the desired product. The mole of unsaturation in oleic acid is set at 1 mole while the amount of hydrogen peroxide and formic acid is varied. In a prefered embodiment of the present invention, the amount of hydrogen peroxide and formic acid falls in between 1 mole to 1.2 moles and 0.40 moles to 1 mole respectively against 1 mole of unsaturation in oleic acid.

Meanwhile, a catalyst preferably sulphuric acid is added to facilate the hydroxylation process. Anyway the reaction could also be carried out in the absence of catalyst.

The di- or polyhydroxy fatty acids that produced according to the present invention is non irritant and suitable to be used in cosmetic products.

In this invention, it is advisable to follow the sequence of adding the reactants, which can affect the final product. The full amount of oleic acid, formic acid and sulphuric acid are added to a reactor, followed by about 15% of the required amount of hydrogen peroxide. This mixture of reactants is then stirred to produce a homogeneous mixture. As the stirring continued, an increase in the temperature of the mixture is observed. This phenomenon is caused by two exothermic reactions taking place in the reactor, whereby formic acid and hydrogen peroxide react to produce performic acid 'in-situ', followed by the reaction between performic acid and the double bond (C═C) of the unsaturated fatty acid. When a slight drop in the reaction temperature is observed, the remaining amounts of hydrogen peroxide are added dropwisely, with constant stirring.

The temperature of the reaction maintained in behavior room temperature to maximum 90° C. Initially, no heat is supplied, as the reactions occurring are highly exothermic. It is observed that reaction progressed, the temperature increased from room temperature to about 60° C. and then after a while it decreased slightly. After this point, the remaining hydrogen peroxide are added slowly to the mixture and the temperature is maintained between about 80° C. to 90° C. through out the reaction by applying heat when necessary. The temperature range of about 80° C. to 90° C. is found to be the optimum temperature for the reaction.

According to the present invention, the duration of the reaction is within 3 to 6 hours depending on the oxirane oxygen content (OOC) of the reaction mixture. However, it is advisable to carry out the reaction until the OOC value is less than 0.05.

In this invention, the reaction product is subjected to a sequence of product work-up. First of all, the reaction product is poured into a separatory funnel and allowed to settle until two layers of product are observed. The lower layer is the spent acid while the top layer is the desired product. Therefore, the spent acid, which comprises hydrogen peroxide, formic acid, performic acid and other impurities, is then drained out while the desired product is left to solidity. Later on, the solidified product is washed with adequate amount of chilled water (about 5° C. to 10° C.) until the pH of washing water and product are in the range of 2.5 to 3.0. Avoid washing the product while it is still in liquid form, other wise an emulsion will form causing some difficulty in carrying out the procedure.

After the washing process, the product is dried under vacuum at 0.1 bar and at temperature 70° C. The moisture level in the product was kept below 3% for easy purification of the product, which will be discuss in the following description.

The product acquired after the washing and drying steps are referred to as crude DHSA and its properties are shown in Table 2. The crude DHSA yield falls in the range of about 79% to 98%.

TABLE 2

The properties of crude DHSA

| Parameters | Range |
|---|---|
| Iodine Value (g $I_2$/100 g sample) | <15 |
| Melting Point (° C.) | 75-79 |
| Purity by GC (%) | 60-70 |
| Hydroxy Value (mg KOH/g sample) | 180-230 |
| Yield (%) | 74-90 |

The present invention also provides a process for purifying DHSA in admixture with some free fatty acid, plus other impurities, involving the process step of recrystallization. Polar solvents such as ethanol, isopropyl alcohol (IPA), acetone and ethyl acetate are used in the recrystallization. Solvents are used as 100% or in combination with about 10% to 30% water. The ratios between samples to solvent are in the range of about 1:1 to 1:5.

In the recrystallization technique, the crude DHSA is dissolved in the solvent with a slight heating of the mixture (about 50° C. to 60° C.). The solution is left to cool down gradually to ambient temperature and further cooled at about 10° C. to 15° C. to ensure maximum yield. The precipitate obtained is filtered and dried. The product referred to, as purified palm DHSA is a white powdery solid with waxy sensation. The product is non-irritant and its properties are shown in Table 3. The non-irritancy properly was conducted through in vitro derived skin irritection study.

TABLE 3

The properties of purified DHSA by crystallization.

| Parameters | Range |
|---|---|
| Iodine Value (g $I_2$/100 g sample) | <3 |
| Melting Point (° C.) | 85-92 |
| Purity by GC (%) | 75-80 |
| Hydroxyl Value (mg KOH/g sample) | 270-310 |
| Yield | 35-45 |

According to the present invention, preferably hexane is used to purify the crude DHSA, besides the recrystallization method with polar solvents. Hexane is chosen because it is a food grade solvent. Washing with hexane resulted in a good yield of purified DHSA. Found to be easier process than the recrystallization method. The ratios of crude DHSA and hexane are in the range of 1:1 to 1:2. Cooled hexane (about 10° C. to 15° C.) is used in order to minimize the solubility of crude DHSA in hexane.

In the washing process, the crude DHSA is melted at temperature 75° C. to 80° C. Then, cooled hexane is added slowly to DHSA, the liquid with stirring until the formation of DHSA precipitates. The precipitate is filtered and this process is repeated at least twice. The purified DHSA is a white powdery solid with waxy sensation, and it is non-irritant. The properties of the purified DHSA are shown in Table 4.

TABLE 4

The properties of the purified DHSA by washing with hexane.

| Parameters | Range |
|---|---|
| Iodine Value (g $I_2$/100 g sample) | <3 |
| Melting Point (° C.) | 85-92 |
| Purity by GC (%) | 70-75 |
| Hydroxy Value (mg KOH/g sample) | 250-290 |
| Yield (%) | 50-55 |

EXAMPLE

Example 1

Synthesis of Crude DHSA

The full amount of oleic acid (250 g, 0.94 mole of unsaturation), formic acid (43.2 g, 0.94 mole) and sulphuric acid (0.5 g, 0.2%) were added to a reactor, followed by 15% of total amount of the required hydrogen peroxide (11 g, 1.08 moles). This mixture of reactants was homogenize by stirring. As the stirring was carried out, an increase in temperature was observed, where the temperature of the mixture has risen from 25° C. to 60° C. When the temperature started to decrease (55° C.), the remaining amount of hydrogen peroxide (62.6 g), (total 1.08 moles) was then-added drop-wise with continuous stirring.

The temperature of the reaction was maintained between 80-90° C., by applying heat if necessary. The reaction was allowed to take place for 5 hours and the OOC is analyzed until it is less than 0.05.

Example 2

The reaction product from example 1 was poured into a separatory funnel and allowed to settle. The bottom spent acid layer was removed and the top upper organic layer was washed with chilled (5° C. to 10° C.) water until the pH of washing water and product were in the range of 2.5 to 3.0. The washed crude DHSA was dried under vacuum at 0.1 bar and at temperature 70° C. and its properties are shown in table 5.

TABLE 5

The properties of crude DHSA

| Parameters | Value |
|---|---|
| Iodine Value (g $I_2$/100 g sample) | 2.5 |
| Melting Point (° C.) | 79 |
| Purity by GC (%) | 65 |
| Hydroxyl Value (mg KOH/g sample) | 214 |
| Yield (%) | 79 |

Example 3

Example 1 was repeated but the amount of formic acid used was 0.4 moles instead of 0.94 moles. The properties of the crude DHSA obtained were shown in Table 6.

TABLE 6

The properties of crude DHSA

| Parameters | Value |
| --- | --- |
| Iodine Value (g I$_2$/100 g sample) | 13.3 |
| Melting Point (° C.) | 75 |
| Purity by GC (%) | 60 |
| Hydroxyl Value (mg KOH/g sample) | 228 |
| Yield | 74 |

Example 4

Example 1 was repeated but the amount of hydrogen peroxide was reduced to 0.94 mole instead 1.08 moles. The properties of the crude DHSA were shown in Table 7.

TABLE 7

The properties of crude DHSA

| Parameters | Value |
| --- | --- |
| Iodine Value (g I$_2$/100 g sample) | 10 |
| Melting Point (° C.) | 75 |
| Purity by GC (%) | 65 |
| Hydroxyl Value (mg KOH/g sample) | 214 |
| Yield (%) | 78 |

Example 5

Purification of Crude DHSA Via Recrystallization Method

In this trial, 50 g of crude DHSA (from example 1) was used and it was dissolved in 37.5 ml of ethanol with slight heating (50° C. to 60° C.) of the mixture. The solution was left to cool gradually to ambient temperature and further cooled at 10° C. to 15° C. The purified DHSA precipitate was filtered and dried to give white powdery with waxy sensation. The properties are shown in Table 8.

TABLE 8

The properties of purified DHSA via recrystallisation with ethanol

| Parameters | Value |
| --- | --- |
| Iodine Value (g I$_2$/100 g sample) | 1.8 |
| Melting Point (° C.) | 89.7 |
| Purity by GC (%) | 80 |
| Hydroxyl Value (mg KOH/sample) | 306.9 |
| Yield | 40 |

Example 6

Example 4 was repeated but the solvent used was a mixture of ethanol and water with ratio of 80:20. The properties of the purified DHSA are shown in Table 9.

TABLE 9

The properties of purified DHSA

| Parameters | Value |
| --- | --- |
| Iodine Value (g I$_2$/100 g sample) | 2.5 |
| Melting Point (° C.) | 85.8 |
| Purity by GC (%) | 75 |

TABLE 9-continued

The properties of purified DHSA

| Parameters | Value |
| --- | --- |
| Hydroxyl Value (mg KOH/g sample) | 272.5 |
| Yield | 35 |

Example 7

Example 4 was repeated but with another solvent, which is isopropyl alcohol (IPA) instead of ethanol. The properties of the purified DHSA are shown in Table 10.

TABLE 10

The properties of purified DHSA via recrystallisation with isopropyl alcohol

| Parameters | Value |
| --- | --- |
| Iodine Value (g I$_2$/100 g sample) | 2.5 |
| Melting Point (° C.) | 87.9 |
| Purity by GC (%) | 80 |
| Hydroxyl Value (mg KOH/g sample) | 282.2 |
| Yield (%) | 40 |

Example 8

Example 6 was repeated but the solvent used was a mixture of isopropyl alcohol (IPA) and water with ratio of 80:20. The properties of the purified DHSA are shown in Table 11.

TABLE 11

The properties of purified DHSA

| Parameters | Value |
| --- | --- |
| Iodine Value (g I$_2$/100 g sample) | 2.7 |
| Melting Point (° C.) | 86.6 |
| Purity by GC (%) | 75 |
| Hydroxyl Value (mg KOH/g sample) | 298.4 |
| Yield (%) | 35 |

Example 9

Purification of Crude DHSA Via Washing with Hexane Method

Ratio between crude DHSA and hexane was 1:2. In this trial, 100 ml of chilled hexane (10-15° C.) were added to 50 g melted of crude DHSA. The mixture was then cooled until the formation of DHSA precipitate. The precipitate was filtered and this process was repeated at least twice. The purified DHSA was white powdery with waxy sensation. The properties of the purified DHSA are shown in Table 12.

TABLE 12

The properties of the purified DHSA with hexane

| Parameters | Value |
| --- | --- |
| Iodine Value (g I$_2$/100 g sample) | 2.7 |
| Melting Point (° C.) | 85 |
| Purity by GC (%) | 74 |

TABLE 12-continued

The properties of the purified DHSA with hexane

| Parameters | Value |
|---|---|
| Hydroxy Value (mg KOH/g sample) | 250 |
| Yield (%) | 55 |

It is to be understood that the present invention may be embodied in other specific forms and is not limited to the sole embodiment described above. However modification and equivalents of the disclosed concepts such as those which readily occur to one skilled in the art are intended to be included within the scope of the claims which are appended thereto.

The invention claimed is:

1. An improved method for the hydroxylation of palm based oleic acid comprising the steps of:
    (a) reacting palm based oleic acid, formic acid, and 15% of the required amount of hydrogen peroxide in the presence of a catalyst at increased reaction temperature;
    (b) adding the remaining hydrogen peroxide to maintain the reaction temperature between 80° C. and 90° C. wherein the ratio of said required amount of hydrogen peroxide to formic acid and palm based oleic acid is 1-1.2 moles of hydrogen peroxide to 0.4-1 mole of formic acid and 1 mole of palm based oleic acids.

2. An improved method according to claim 1, wherein said catalyst is sulphuric acid.

3. A method to purify crude hydroxyl fatty acid comprising the steps of:
    (a) heating said crude hydroxyl fatty acid with a solvent or mixture of solvent selected from the group consisting of ethanol, isopropyl alcohol, acetone and ethyl acetate to form a solution;
    (b) cooling said solution to a temperature of 10° C. to 15° C. to form crystallized precipitate; and
    (c) separating said precipitate from the remaining solvent to obtain purified hydroxyl fatty acid.

4. A method according to claim 3, wherein said solvent or mixture of solvent is further mixed with 10 to 30% v/v of water.

5. A method according to claim 3, further comprising the step of drying said separated precipitate.

6. A method according to claim 3, wherein the heating is carried out at a temperature from 50° C. to 60° C.

7. A method according to claim 3, wherein the ratio of crude hydroxyl fatty acid to the solvent or mixture of solvent is 1:1 to 1:5.

8. A method according to claim 4, wherein the ratio of crude hydroxyl fatty acid to the solvent or mixture of solvent is 1:1 to 1:5.

* * * * *